United States Patent
Chiang

(10) Patent No.: US 10,301,841 B2
(45) Date of Patent: May 28, 2019

(54) MOSQUITO REPELLENT AND ANTIBACTERIAL TENT

(71) Applicant: Modus Light, LLC, Overland Park, KS (US)

(72) Inventor: Yu Yun Chiang, Taipei (TW)

(73) Assignee: Modus Light, LLC, Overland Park, KS (US)

( * ) Notice: Subject to any disclaimer, the term of this patent is extended or adjusted under 35 U.S.C. 154(b) by 10 days.

(21) Appl. No.: 15/829,281

(22) Filed: Dec. 1, 2017

(65) Prior Publication Data
US 2018/0334830 A1    Nov. 22, 2018

(30) Foreign Application Priority Data

May 17, 2017 (TW) .............................. 106207068 U

(51) Int. Cl.
| | |
|---|---|
| E04H 15/56 | (2006.01) |
| A01N 31/02 | (2006.01) |
| A01N 43/80 | (2006.01) |
| E04H 15/40 | (2006.01) |
| E04H 15/42 | (2006.01) |
| E04H 15/64 | (2006.01) |
| E04H 15/54 | (2006.01) |
| A01N 25/10 | (2006.01) |

(52) U.S. Cl.
CPC ............. *E04H 15/56* (2013.01); *A01N 25/10* (2013.01); *A01N 31/02* (2013.01); *A01N 43/80* (2013.01); *E04H 15/40* (2013.01); *E04H 15/425* (2013.01); *E04H 15/54* (2013.01); *E04H 15/64* (2013.01)

(58) Field of Classification Search
CPC ......... E04H 15/54; E04H 15/36; E04H 15/56; E04H 15/02; E04H 15/40; E04H 15/425; E04H 15/42; A01N 43/80

USPC .......................... 135/124, 137, 156, 115, 116
See application file for complete search history.

(56) References Cited

U.S. PATENT DOCUMENTS 4,265,259 A * 5/1981 Gillis .................... E04H 15/425
                                                         135/115
5,628,336 A * 5/1997 Lee ......................... E04H 15/42
                                                         135/114

(Continued)

FOREIGN PATENT DOCUMENTS

JP          06235172 A * 8/1994 ............. A01N 25/34

OTHER PUBLICATIONS

CN 205777866 U, Dec. 7, 2016, Title: Multifunctional tent has thermal layer bonded on base layer, anti-mosquito layer formed on warm-keeping layer through coating adhesive. , Drawing p. 1. (Year: 2016).*

*Primary Examiner* — Winnie Yip
(74) *Attorney, Agent, or Firm* — Erise IP, P.A.

(57) ABSTRACT

A mosquito repellent and antibacterial tent includes a tent body, a first support bar and a second support bar. The tent body is formed by a base fabric entirely provided with a mosquito repellent agent and a waterproofing agent. An adhesive coating layer is provided on the base cloth. The tent body includes a plurality of first positioning parts. A side surface of the tent body has at least one opening. The first support bar and the second support bar are connected to the plurality of first positioning parts so as to be crossed to support the tent body. Thus, the mosquito repellent and antibacterial tent achieves mosquito repellent and antibacterial effects as well as being waterproof and sturdy.

18 Claims, 2 Drawing Sheets

(56) References Cited

U.S. PATENT DOCUMENTS

| | | | | |
|---|---|---|---|---|
| 6,470,901 | B1* | 10/2002 | Scherer | E04H 15/322 |
| | | | | 135/121 |
| 6,672,323 | B2* | 1/2004 | Gupta | E04H 15/40 |
| | | | | 135/126 |
| 7,823,600 | B2* | 11/2010 | Laakso | E04H 15/64 |
| | | | | 135/115 |
| 2010/0065094 | A1* | 3/2010 | Ways | E04H 15/34 |
| | | | | 135/96 |
| 2012/0034285 | A1* | 2/2012 | Vestergaard Frandsen | |
| | | | | A01N 43/30 |
| | | | | 424/403 |
| 2016/0083972 | A1* | 3/2016 | Hayes | E04H 15/001 |
| | | | | 135/121 |

* cited by examiner

MOSQUITO REPELLENT AND ANTIBACTERIAL TENT

BACKGROUND OF THE INVENTION

Field of the Invention

The present invention relates to a mosquito and insect repellent and antibacterial tent for outdoor use.

Description of the Related Art

With the rising demand of outdoor recreational activities, camping has become increasingly popular, and the number of camping sites is ever-growing along with such trend. Therefore, tents that are essential for camping also need to continue innovating to meet requirements on leisure quality of modern people.

To be quickly and readily set up, a common conventional tent usually has a rather simple framework, which hardly satisfies criteria of being totally waterproof, windproof and sturdy. Further, an outdoor environment with high humidity is susceptible to the growing of mosquitoes, insects and bacteria, and all types of activities conducted under such conditions are prone to invasions of all sorts of bacteria, mosquitoes and insects, causing infections or physical discomforts and hence lowered body functions that may lead to various undesirable consequences. Carrying large amounts of mosquito repellent and/or sterilization supplies and devices is quite unrealistic and inconvenient for outdoor campers. In summary, with respect to designs of conventional tents, in addition to lacking adequate waterproofness, windproofness and sturdiness, very few of those designs can provide antibacterial as well as mosquito and insect repellent effects.

Therefore, the architecture of a tent needs to have a sturdy and windproof framework design, which at the same time should withstand a humid outdoor environment susceptible to the growing of mosquitoes, insects and bacteria, and provide antibacterial and mosquito repellent effects without relying on complicated mosquito repellent and sterilization supplies. However, most commercially available tents use simple support structure for quick assembling or require a large amount of securing elements in order to be waterproof, windproof and sturdy, which render assembly process time-wasting and effort-consuming. For users who further demand mosquito and insect repellent effects, supplies or accessories usually need to be separately purchased.

Therefore, there is a need for related industrialists to provide an ideal, practical and innovated solution to solve the problems of conventional tents to meet requirements of consumers.

SUMMARY OF THE INVENTION

In view of the above problems, the present various embodiments of the invention provide advantages that include some or all of the following: they comprise a more simple, convenient and advanced design for eliminating the above problems. The solution of the present invention includes a simple assembly process for achieving greater benefits and at the same time attends to application flexibilities and economical considerations.

The problems to be solved in various embodiments of the present invention are: 1) a simple structure of a conventional tent fails to provide waterproof and windproof structure as well as sturdiness; 2) a structure of a conventional tent that has a sturdy structure and provides waterproof and windproof effects usually has complicated parts and a complex assembly process; and 3) a conventional tent needs to be used with additional mosquito repellent and antibacterial products in order to achieve repellent and antibacterial effects.

To solve the foregoing problems, the present invention is targeted at achieving effects of: 1) effectively improving windproofness and sturdiness of a tent by a combined provision of a support bar and a reinforcing support; 2) by positioning parts fixedly disposed on a fabric of the tent, enabling the tent to be simply and readily assembled and set up without involving complicated parts; and 3) achieving effective waterproofing by applying an adhesive coating layer on the fabric of the tent and further providing mosquito repellent and antibacterial results using the fabric combined and treated with effective mosquito repellent and antibacterial agents, thus providing an effective protection method for mosquito repellent and antibacterial effects.

To further describe and solve the problems of the prior art and to achieve the expected results, the present invention provides a mosquito repellent and antibacterial tent comprising a tent body. The tent body is formed by a base cloth entirely provided with a mosquito repellent agent and a waterproofing agent. An adhesive coating layer is provided on the base cloth. The tent body includes a plurality of positioning parts. A side surface of the tent body has at least one opening. The mosquito repellent and antibacterial tent further includes a first support bar and a second support bar. The first support bar and the second support bar are connected to the plurality of positioning parts to be cross unfolded during assembly to support the tent body.

In one embodiment, the mosquito repellent and antibacterial tent of the present invention further includes a plurality of second positioning parts, a first reinforcing support and a second reinforcing support. The plurality of second positioning parts are connected on the tent body. The first reinforcing support and the second reinforcing support are respectively connected to the second positioning parts so as to be crossed symmetrically on the tent body, each in an inverted U-shape.

In one embodiment, the adhesive coating layer includes coating glue, which includes a polyurethane coating glue, N,N-dimethylformamide, a bridging agent and an antibacterial agent.

The above and other aspects of the invention will become better understood with regard to the following detailed description of the preferred but non-limiting embodiments. The following description is made with reference to the accompanying drawings.

DETAILED DESCRIPTION OF THE INVENTION

Figure 1:
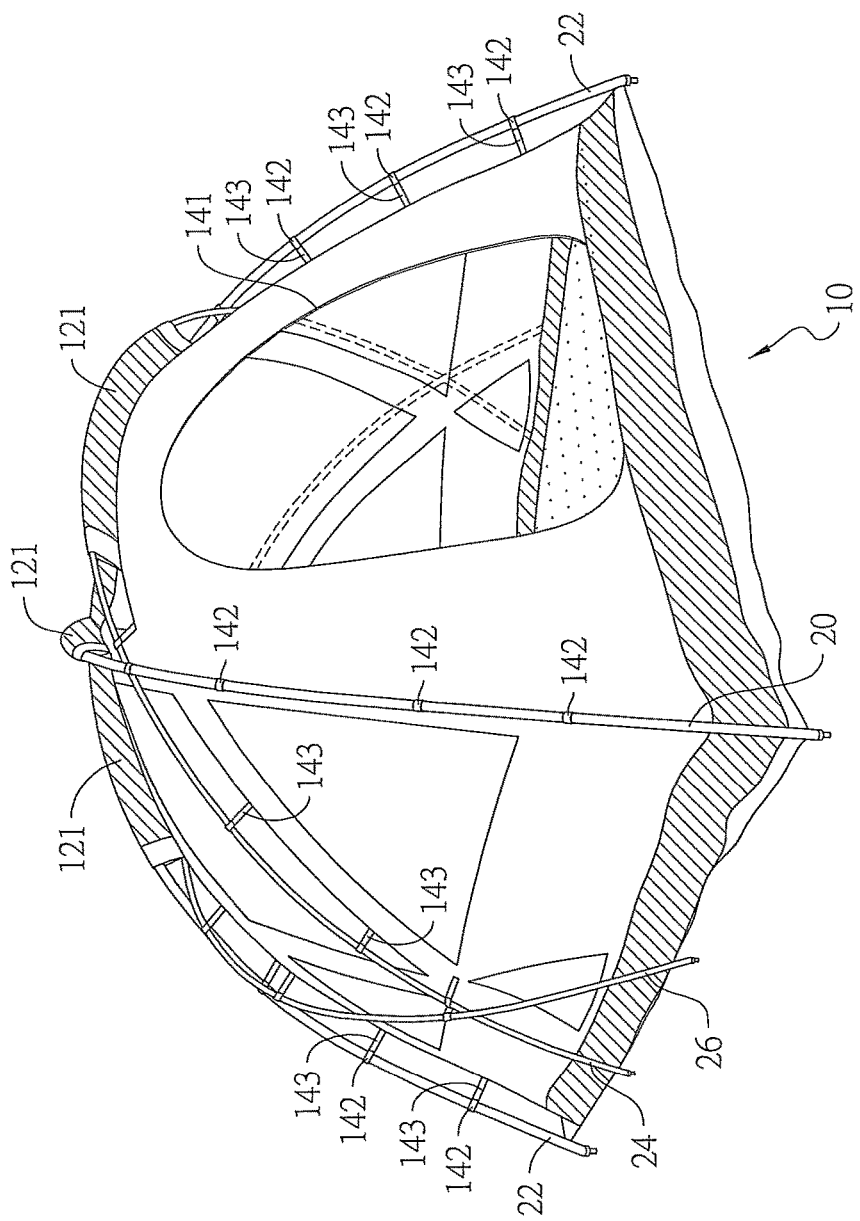
FIG. 1 is a perspective view of a tent body according to an embodiment of the present invention.

FIG. 1 illustrates a tent body 10 according to an embodiment of the present invention. A mosquito repellent and antibacterial tent of the present invention includes the tent body 10, which is formed by a base cloth 32 preferably entirely covered by or incorporating a mosquito repellent agent and a waterproofing agent. An adhesive coating layer 34 is provided on the base cloth 32. An outer surface of the tent body 10 has a plurality of knot tapes, each of which serves as a first positioning part 121. In implementation, the first positioning part 121 may also be a wrapper for positioning purposes. A side surface of the tent body 10 has at least one opening 141. The mosquito repellent and antibacterial tent further includes a first support bar 20 and a second support bar 22. The first support bar 20 and the second support bar 22 are connected to the plurality of first positioning parts 121 to be crossed in an unfolded configuration to support the tent body 10.

Figure 2:
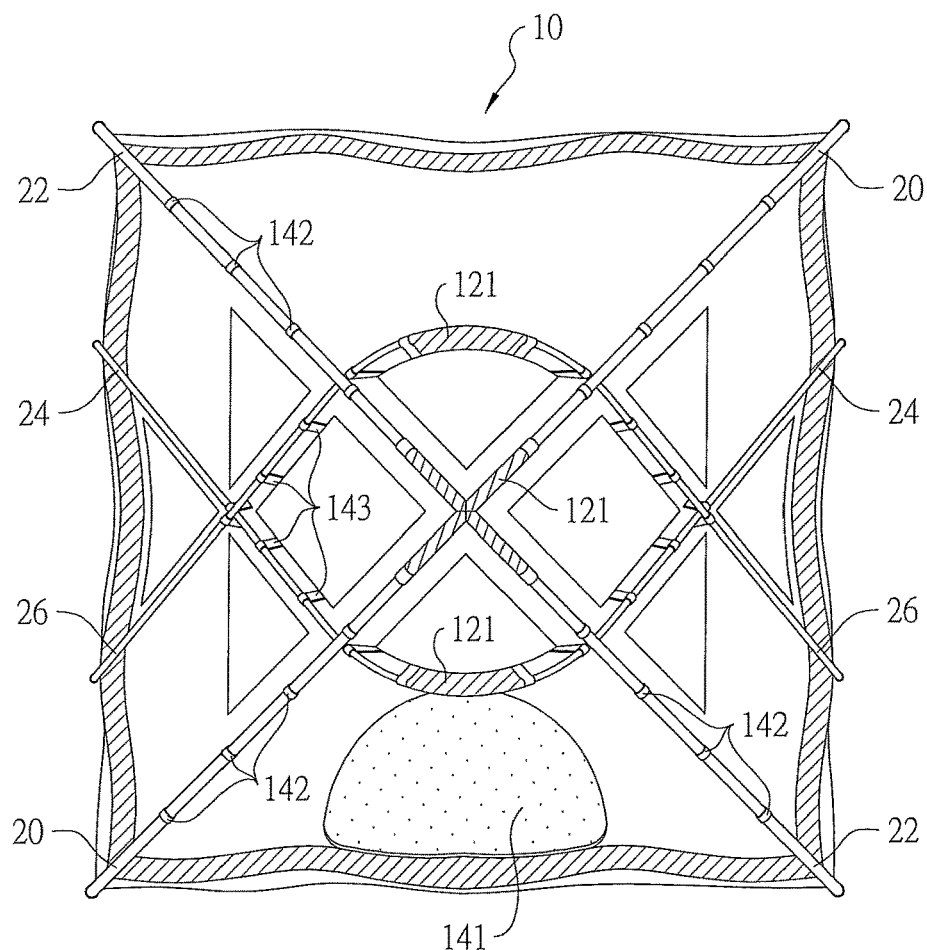
FIG. 2 is a top view of a tent body according to an embodiment of the present invention.

FIG. 2 shows a top view of the tent body 10 according to an embodiment of the present invention. The mosquito repellent and antibacterial tent further includes a plurality of second positioning parts 142 and 143, a first reinforcing support 24 and a second reinforcing support 26. The second positioning parts 142 and 143 are knot tapes, or wrappers for positioning purposes. The plurality of second positioning parts 142 and 143 are connected on the tent body 10. The first reinforcing support 24 and the second reinforcing support 26 are respectively each connected with the plurality of second positioning parts 142 and 143 so as to be crossed symmetrically with one another on the tent body 10 in an inverted U-shape.

Figure 3:
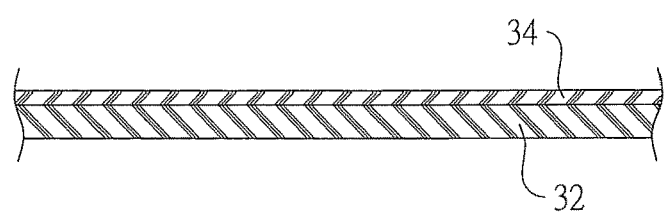
FIG. 3 is a schematic and cross sectional view of a base cloth according to an embodiment of the present invention.

As shown in FIG. 3, in one embodiment, the tent body 10 is formed by the base cloth 32. The base cloth 32 is covered by the adhesive coating layer 34 and is treated with a mosquito repellent treatment with an added mosquito repellent agent during a padding process performed by a fabric forming machine during manufacture. The amount of the mosquito repellent agent added is 4% to 6% to the fabric weight and drying is performed under a temperature of 130° C. to 150° C. During the padding process performed by a fabric forming machine, the base fabric 32 is also treated with a waterproofing treatment with an added waterproofing agent. The amount of the waterproofing agent added is 4% to 6% to the fabric weight, and drying is performed under a temperature of 140° C. to 180° C.

The base cloth 32 of the tent body 10 is preferably a polyester lattice cloth, and is added with a mosquito repellent agent made of an NK-10 natural geraniol marketed under the trademark Greenfirst™ (the Greenfirst™ product series is mosquito and insect repellent products of BREYNER). The adhesive coating layer 34 covering the base cloth 32 is an oily polyurethane coating and includes 70% to 80% polyurethane coating, 10% to 20% N, N-dimethylformamide, 5% to 8% bridging agent, and 0.05% to 2% antibacterial agent.

The above NK10 product is an all-natural plant antiparasitic auxiliary agent, PROFYL NK10 is a mosquito and insect repellent auxiliary agent, and geraniol is a main active substance of a finishing agent of NK10. These substances are essences extracted from plant, so as to offer various benefits, be effectively biodegradable, and be in balance with the environment, as well as provide performance and safety perspectives. NK10 has an environmental effective degradation rate of 95%, and is verified by Oeko-Tex, making NK10 a safe and environmental friendly chemical mosquito and insect repellent auxiliary agent.

After completing the two processes of the mosquito repellent treatment and the waterproofing treatment, a coating process is performed on the mosquito repellent treated and waterproof treated base cloth 32. For the formula of the adhesive coating layer, the coating glue is preferably a common solvent-based polyurethane coating glue, which has a good bonding performance and can easily form a cross-linking reaction with a fabric. Further, the solvent-based polyurethane coating glue is more durable than a water-based polyurethane, with the preferred amount applied being in the range from 10 g/m$^2$ to 40 g/m$^2$.

The foregoing antibacterial agent is an antibacterial agent from a product marketed under the trademark Ultra-Fresh™ of Thomson Research Associates, a Canadian organization. The model of the antibacterial agent adopted in the present invention is Ultra-Fresh DM25, which is an antimicrobial, antifungal and antimite antibacterial agent that is registered in and verified by the U.S. Environmental Protection Association (EPA). Ultra-Fresh DM25 is an antibacterial agent in a solvent-based carrier. In one preferred embodiment, the antibacterial agent is suitable in products such as a solvent-based polyurethane coating, polyvinyl chloride and foam sponges.

The bridging agent is also a polyurethane type bridging agent, and has better compatibility with the polyurethane coating glue and a stronger bonding force, providing an applied fabric with higher resistance against water pressure and excellent application durability. The N, N-dimethylformamide is for diluting the polyurethane glue to an appropriate viscosity. During the coating process, a fixed amount of the solvent-based polyurethane glue, a fixed amount of the antifungal and antibacterial agent DM-25, a fixed amount of the polyurethane bridging agent, and a fixed amount of the N, N-dimethylformamide are prepared into a polyurethane glue to be applied as an adhesive coating layer. The prepared glue is then applied onto the fabric surface by knife coating (a coating device), and the fabric is placed in an oven to dry and completely evaporate the N, N-dimethylformamide from the prepared glue. In one preferred embodiment, the adhesive coating is applied in layers and the number of adhesive coating layers is two to three layers.

In conclusion, based on the disclosure of the application, the present invention achieves the expected results, and provides industrial applicability. While the invention has been described by way of example and in terms of the preferred embodiments, it is to be understood that the invention is not limited thereto. On the contrary, various modifications and similar arrangements and procedures, regarded as equivalences of the concept of the invention, can be deduced based on the disclosure of teaching of the description, and the scope of the appended claims therefore should be accorded the broadest interpretation so as to encompass all such modifications and similar arrangements and procedures.

What is claimed and desired to be secured by Letters Patent is as follows:

1. A mosquito repellent and antibacterial tent, comprising:
   a tent body having a top and bottom both formed by a base cloth,
   wherein the base cloth is treated with a mosquito repellent agent,
   wherein the base cloth has a waterproofing adhesive coating layer applied thereon including—
      a polyurethane coating glue,
      a bridging agent, and
      an antibacterial agent,
   wherein the tent body includes a positioning part; and
   a support bar configured to be connected to the positioning part so as to provide structural support to the tent body.

2. The mosquito repellent and antibacterial tent according to claim 1, further comprising:
   a reinforcing support, wherein the tent body further includes a positioning clip,
wherein the reinforcing support is configured to be connected to the positioning clip so as to be crossed symmetrically on the tent body such that reinforcing support has an inverted U-shape in use.

3. The mosquito repellent and antibacterial tent according to claim 1, wherein the polyurethane coating glue is 70% to 80% of the adhesive layer coating.

4. The mosquito repellent and antibacterial tent according to claim 1, wherein the adhesive coating layer is in a range of 10 g/m$^2$ to 40 g/m$^2$.

5. The mosquito repellent and antibacterial tent according to claim 1,
wherein the adhesive coating layer further included N, N-dimethylformamide to dilute the polyurethane coating glue so as to reduce the viscosity,
wherein the N, N-dimethylformamide was evaporated from the adhesive coating layer by drying after application to the base cloth.

6. The mosquito repellent and antibacterial tent according to claim 5, wherein the N, N-dimethylformamide was in a range of 10% to 20% of the adhesive layer coating when applied.

7. The mosquito repellent and antibacterial tent according to claim 1, wherein the bridging agent is a polyurethane type that is compatible with the polyurethane coating glue to provide resistance to water pressure.

8. The mosquito repellent and antibacterial tent according to claim 1, wherein the base cloth is a polyester lattice cloth.

9. The mosquito repellent and antibacterial tent according to claim 1, wherein the base cloth is saturated with the mosquito repellent agent.

10. The mosquito repellent and antibacterial tent according to claim 1, wherein the adhesive layer coating is distinct from the base cloth.

11. The mosquito repellent and antibacterial tent according to claim 1, wherein the mosquito repellent agent is 4% to 6% of the weight of the base cloth.

12. A mosquito repellent and antibacterial tent, comprising:
a base cloth forming a top and bottom of the tent and treated with mosquito repellant agent,
wherein the base cloth was treating with the mosquito repellant agent;
a waterproofing adhesive layer coating distinct from and secured to a side of the base cloth,
wherein the adhesive layer coating includes—
a polyurethane coating glue,
a bridging agent, and
an antibacterial agent.

13. The mosquito repellent and antibacterial tent according to claim 12, wherein the polyurethane coating glue is 70% to 80% of the adhesive layer coating.

14. The mosquito repellent and antibacterial tent according to claim 12, wherein the adhesive coating layer is in a range of 10 g/m$^2$ to 40 g/m$^2$.

15. The mosquito repellent and antibacterial tent according to claim 12,
wherein the adhesive coating layer further included N, N-dimethylformamide to dilute the polyurethane coating glue so as to reduce the viscosity.

16. The mosquito repellent and antibacterial tent according to claim 15, wherein the N, N-dimethylformamide was in a range of 10% to 20% of the adhesive layer coating when applied.

17. The mosquito repellent and antibacterial tent according to claim 13, wherein the bridging agent is a polyurethane type that is compatible with the polyurethane coating glue to provide resistance to water pressure.

18. The mosquito repellent and antibacterial tent according to claim 13, wherein the mosquito repellent agent is 4% to 6% of a final weight of the base cloth.

\* \* \* \* \*